(12) United States Patent
Yaish et al.

(10) Patent No.: US 10,393,893 B2
(45) Date of Patent: Aug. 27, 2019

(54) METHOD AND APPARATUS FOR HIGH ATOMIC NUMBER SUBSTANCE DETECTION

(71) Applicant: Lingacom Ltd., Tel Aviv (IL)

(72) Inventors: David Yaish, Tel Aviv (IL); Yosef Kolkovich, Tel Aviv (IL); Amnon Harel, Haifa (IL)

(73) Assignee: Lingacom Ltd., Tel Aviv (IL)

( * ) Notice: Subject to any disclaimer, the term of this patent is extended or adjusted under 35 U.S.C. 154(b) by 511 days.

(21) Appl. No.: 14/966,086

(22) Filed: Dec. 11, 2015

(65) Prior Publication Data

US 2016/0170072 A1 Jun. 16, 2016

Related U.S. Application Data

(60) Provisional application No. 62/091,090, filed on Dec. 12, 2014, provisional application No. 62/091,021, filed on Dec. 12, 2014.

(51) Int. Cl.
| | |
|---|---|
| *G01N 9/24* | (2006.01) |
| *G01T 1/26* | (2006.01) |
| *G01V 5/00* | (2006.01) |
| *G01V 13/00* | (2006.01) |
| *H05K 3/30* | (2006.01) |
| *G06T 15/00* | (2011.01) |

(52) U.S. Cl.
CPC .............. *G01T 1/26* (2013.01); *G01N 9/24* (2013.01); *G01V 5/005* (2013.01); *G01V 5/0016* (2013.01); *G01V 5/0025* (2013.01); *G01V 5/0033* (2013.01); *G01V 5/0075* (2013.01); *G01V 13/00* (2013.01); *G06T 15/00* (2013.01); *H05K 3/30* (2013.01); *H05K 3/303* (2013.01); *H05K 2201/10151* (2013.01); *Y02P 70/613* (2015.11)

(58) Field of Classification Search
CPC ............................... G01V 5/0008; G01T 1/26
USPC ........................................................ 702/179
See application file for complete search history.

(56) References Cited

U.S. PATENT DOCUMENTS

| | | | |
|---|---|---|---|
| 7,633,062 B2 | 12/2009 | Morris et al. | |
| 7,701,336 B1 * | 4/2010 | Willms | G08B 13/1654 250/390.04 |

(Continued)

OTHER PUBLICATIONS

M. Alexeev et al., "Development of THGEM-based photon detectors for Cherenkov Imaging Counters", JINST—1st International Conference on Micro Pattern Gaseous Detectors, Jun. 2009, IOP Publishing for SISSA.

(Continued)

*Primary Examiner* — Ricky Ngon
(74) *Attorney, Agent, or Firm* — Intrinsic Law Corp.

(57) ABSTRACT

Methods of detecting high atomic weight materials in a volume such as a truck or cargo container are disclosed. The volume is scanned with an X-ray imaging system and a muon detection system. Using the output data of the muon detection system, the exit momentum and incoming and outgoing tracks of each muon are reconstructed. A muon scattering statistical model is calculated using the muon exit momentum and the incoming and outgoing tracks of the muon. A most likely scattering density map is determined according to the muon-scattering statistical model and an X-ray statistical model. A visual representation of the most likely scattering density map is displayed.

32 Claims, 13 Drawing Sheets

(56) References Cited

U.S. PATENT DOCUMENTS

| | | | |
|---|---|---|---|
| 7,945,105 B1 | 5/2011 | Jaenisch | |
| 8,288,721 B2* | 10/2012 | Morris | G01T 1/18 |
| | | | 250/251 |
| 2008/0315091 A1* | 12/2008 | Morris | G01T 1/18 |
| | | | 250/307 |
| 2014/0332685 A1* | 11/2014 | Anghel | G01N 23/046 |
| | | | 250/307 |
| 2015/0108349 A1* | 4/2015 | Bendahan | G01V 5/0016 |
| | | | 250/306 |

OTHER PUBLICATIONS

A. Ochi et al., "Micro Pixel Chamber with resistive electrodes for spark reduction", Oct. 22, 2013.

G. Wang et al., "Bayesian Image Reconstruction for Improving Detection Performance of Muon Tomography", IEEE Transactions on Image Processing, May 2009, p. 1080-89, vol. 18, No. 5, IEEE.

C. L. Morris et al., "Horizontal cosmic ray muon radiography for imaging nuclear threats", Nuclear Instruments and Methods in Physics Research, 2014, p. 42-46, B330, Elsevier.

K. N. Borozdin, "Radiographic imaging with cosmic-ray muons", Nature, Mar. 20, 2003, p. 277, vol. 422, Nature Publishing Group.

A. Clarkson et al., "GEANT4 Simulation of a Scintillating-Fibre Tracker for the Cosmic-ray Muon Tomography of Legacy Nuclear Waste Containers", Sep. 2013, p. 1-11.

J. Armitage et al., "First Images from the Cript Muon Tomography System", Applications of Nuclear Techniques, International Journal of Modern Physics: Conference Series, Feb. 2014, vol. 27, World Scientific.

F. Sauli, "Gas Electron Multiplier (GEM) Detectors: Principles of Operation and Applications", Comprehensive Biomedical Physics, vol. 6.

W. B. Gilboy et al., "Industrial radiography with cosmic-ray muons: A progress report", Nuclear Instruments and Methods in Physics Research, May 2007, p. 785-787, No. 580, Elsevier B.V.

S. Riggi et al., "Muon tomography imaging algorithms for nuclear threat detection inside large volume containers with the Muon Portal detector".

K. Gnanvo et al., "Imaging of high-Z material for nuclear contraband detection with a minimal prototype of a Muon Tomography station based on GEM detectors".

H. M. Jaenisch et al, "Real Time Muon Tomography Imaging Simulation and Fast Threat Target Identification", Proc. of SPIE, 2009, vol. 7310, SPIE.

K. Gnanvo et al., "Large Size GEM for Super Bigbite Spectrometer (SBS) Polarimeter for Hall A 12 GeV program at JLab", Nuclear Inst. and Methods in Physics Research.

C. L. Morris et al., "Tomographic Imaging with Cosmic Ray Muons", Science and Global Security, 2008, p. 37-53, No. 16, Taylor & Francis Group LLC.

K. Gnanvo et al., "Detection and Imaging of High-Z Materials with a Muon Tomography Station Using GEM Detectors", 2010.

C. L. Morris et al., "Obtaining material identification with cosmic ray radiography", AIP Advances, 2012, AIP Publishing.

M. S. Mitra et al., "Empirical expressions for angular deviation of muons transmitted through slabs of iron, lead and uranium", Nuclear Instruments and Methods in Physics Research A, 2009, p. 684-693, No. 604, Elsevier B.V.

M. Benettoni et al., "Noise reduction in muon tomography for detecting high density objects", Dec. 2013.

R. Oliveira et al., "First Tests of Thick GEMs with Electrodes Made of a Resistive Kapton", Jan. 11, 2007.

S. Pesente et al., "First results on material identification and imaging with a large-volume muon tomography prototype", Nuclear Instruments and Methods in Physics Research A, 2009, p. 738-746, No. 604, Elsevier B.V.

"The New Detector Concept: Properties of Solid Neutron Converters; The Challenge with Insufficient Detection Efficiency; The GEM, a Substrate Transparent to Charges; CASCADE: the Efficient High-Rates Area-Detector for Neutrons", Universitat Heidelberg, www.physi.uni-heidelberg.de/Forschung/ANP/Cascade/Konzept/?lang=en.

G. Wang et al., "Statistical Image Reconstruction for Muon Tomography Using a Gaussian Scale Mixture Model", IEEE Transactions on Nuclear Science, Aug. 2009, p. 2480-86, vol. 56, No. 4, IEEE.

M. Byszewski et al., "Resistive-strips micromegas detectors with two-dimensional readout", 2nd International conference on Micro Pattern Gaseous Detectors, Aug. 29-Sep. 1, 2011, IOP Publishing for SISSA.

G. Bencivenni et al., "The Resistive-WELL detector: a compact spark-protected single amplification-stage MPGD", 2014.

A. Di Mauro et al., "Development of innovative micropattern gaseous detectors with resistive electrodes and first results of their applications", 2007.

A. G. Agocs et al., "Study of GEM-like detectors with resistive electrodes for RICH applications", 2007.

R. C. Hoch, "Advances in Cosmic Ray Muon Tomography Reconstruction Algorithms", 2009, Florida Institute of Technology.

D. G. Underwood et al., "RPC Investigation Using Finely Spaced 2-D Strip Readout", IEEE Nuclear Science Symposium Conference Record, 2007, p. 618-622, IEEE.

L. J. Schultz, "Cosmic Ray Muon Radiography", 2003, Portland State University.

S. J. Stanley et al., "See inside: The development of a cosmic ray muon imaging system to aid the clean up of the UK's nuclear waste legacy", Annals of Nuclear Energy, 2008, p. 507-17, No. 35, Elsevier.

L. J. Schultz et al., "Statistical Reconstruction for Cosmic Ray Muon Tomography", IEEE Transactions on Image Processing, Aug. 2007, p. 1985-1993, vol. 16, No. 8, IEEE.

C. Cantini et al., "Long-term operation of a double phase LAr LEM Time Projection Chamber with a simplified anode and extraction-grid design", 2013.

L. Yuanyuan et al., "Imaging Algorithms for Cosmic Ray Muon Radiography Detection of Nuclear Materials", Tsinghua Science and Technology, Jun. 2009, p. 313-321, vol. 14, No. 3.

* cited by examiner

METHOD AND APPARATUS FOR HIGH ATOMIC NUMBER SUBSTANCE DETECTION

RELATED APPLICATIONS

This application claims the benefit of and priority to U.S. Provisional Application No. 62/091,090, entitled "Method and Apparatus for High Atomic Number Substance Detection," filed on Dec. 12, 2014. This application also claims the benefit of and priority to U.S. Provisional Application No. 62/091,021, entitled "Large Scale Gas Electron Multiplier and Detection Method," filed on Dec. 12, 2014. Each application is incorporated herein by reference.

The claimed invention was made as a result of activities undertaken within the scope of the joint research agreement between Rapiscan Laboratories, Inc. and Lingacom LTD.

TECHNICAL FIELD

The present application relates to detection of substances having high atomic numbers (Z). Specifically, the application discloses detectors and method for detection of such substances at relatively large scales such as in industrial and security applications, using muon interactions and resulting particle interactions for said detectors and detection, as well as methods to be used in interpreting said interactions in conjunction with additional measurements of the same scanned volume, such as X-ray images.

BACKGROUND

Detectors for high atomic number materials are used at shipping ports to search for radioactive and nuclear materials that may be hidden in shipping containers. In general, a shipping container may first pass through a radiation portal monitor, which is essentially a Geiger counter, to detect any unshielded nuclear matter, such as Uranium. However, lead and other dense materials can be used to smuggle radioactive and nuclear materials through radiation portal monitors by shielding the radioactive radiation emitted from the nuclear matter.

To detect Shielded Nuclear Material (SNM), the container may next pass through an X-ray detector. The X-ray detector is used to look for dense materials, such as lead, that may be in the shipping container. If the shipping container does not include a dense material, an X-ray image of the shipping container will be bright since the X-rays can pass through the goods in the shipping container. However, if the shipping container includes lead or other dense materials, the X-ray image will include a corresponding dark area since the X-rays cannot pass through the dense material. Thus, the detection of high-density materials by X-ray is an indicia that the shipping container contains SNM or other shielded contraband.

If the X-ray image provides such an indicia, the shipping container is taken to a muon scattering detector for further inspection. A muon scattering detector can be used to reconstruct a three-dimensional image of a volume, for example based on deflections and scattering angles of the muons as measured by planar detectors located above and below the shipping container. A threat detection algorithm can be used to automatically raise an alarm based on the resulting three-dimensional image.

Currently the information provided by the X-ray detector and the muon scattering detector is analyzed separately. It would be desirable to combine the information from the detectors to improve the sensitivity of the detection system.

The angular scattering of a muon as it transverses a thin layer of material of thickness L and scattering density $\lambda$, is conveniently described in terms of the scattering angle in a plane vertical to the layer. The average scattering angle is zero, and the distribution of scattering angles around this average can be approximated to a Gaussian distribution of width $$\sigma = \frac{\sqrt{\lambda L}}{\beta p},$$

where $\beta$ and p are the velocity of the muon as a fraction of the speed of light and the (magnitude of the) momentum of the muon. Over 95% of the scattering events are well described by this approximation. Since muons with energies below ~0.3 GeV are unlikely to be measured, in practice the denominator is roughly equal to the momentum, and thus the muon's momentum sets the scale of the scattering. In addition to angular scattering, the muon may also be deflected to the sides by its interactions with the material. The muon momentum also sets the scale of such deflections, and of their correlations with the angular scattering.

The scattering density $\lambda$ increases with the atomic number Z. A useful approximation is $$\lambda = C\frac{\rho}{A}(11.39 - \ln Z)Z(Z+1),$$

where C is a constant, $\rho$ is the mass density of the material, and A its atomic weight. For solids and liquids, $\rho$ tends to grow together with A, though the correlation is a rough one. The mass of common cargos is dominated by elements with $Z \geq 6$, and of course $Z \leq 94$, so that the term in parenthesis changes slowly and $\lambda$ increases almost as fast as $Z^2$. Hence muon scattering is particularly sensitive to high-Z materials.

The expected energy loss of a muon as it passes a distance of $\Delta x$ in a given material is $\Delta E = P_s \rho \Delta x$, where $P_s$ is the stopping power of the material (the symbol $$\frac{dE}{dx}$$

is often used in the literature instead of $P_s$) and $\rho$ its mass density. The actual energy loss is distributed asymmetrically around this value, with a distribution often modeled by the Bethe-Bloch formula.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

In an aspect, the invention is directed to a method of detecting a high-Z material in a volume. The method includes scanning the volume with an X-ray imaging system to provide X-ray imaging data. The method also includes scanning the volume with a muon detection system to provide muon scan data. The method also includes using the muon scan data, reconstructing an exit momentum and incoming and outgoing tracks of muons that pass through the muon detection system, the incoming track including a first position and first direction of travel of the muons before the muons enter the volume, the outgoing track including a second position and a second direction of travel of the muons after the muons exit the volume, the exit momentum reconstructed for the muons after the muons exit the volume. The method also includes calculating a muon-scattering statistical model using (a) the muon exit momentum and (b) the incoming and outgoing tracks of the muon. The method also includes calculating from the X-ray imaging data an X-ray statistical model suitable for use in conjunction with the muon-scattering statistical model; determining a most likely scattering density map according to the muon-scattering and X-ray statistical models. The method also includes displaying a visual representation of the most likely scattering density map on a display.

IN THE DRAWINGS

For a fuller understanding of the nature and advantages of the present invention, reference is be made to the following detailed description of preferred embodiments and in connection with the accompanying drawings, in which.

DETAILED DESCRIPTION

Figure 1:
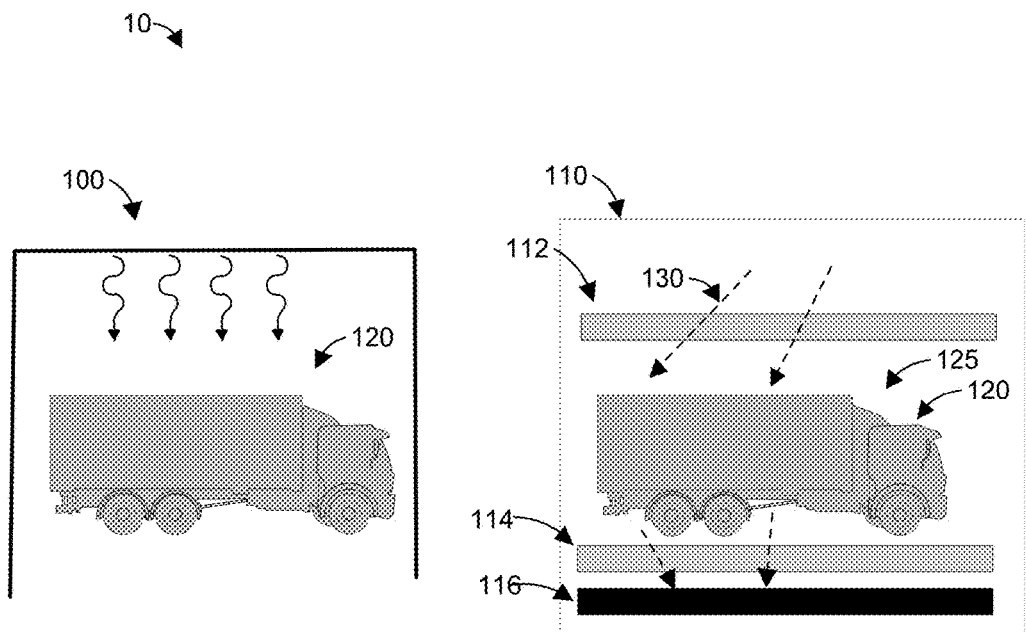
FIG. 1 is a block diagram of a system for detecting high atomic weight materials.

FIG. 1 illustrates a block diagram of a system 10 for detecting high atomic weight (high Z) materials. The system 10 includes a first detector 100 and a muon imaging station 110. The first detector 100 can be an X-ray detector or similar detector capable of detecting high-density materials, such as lead, that may be in a truck 120, a shipping container, etc. If the image generated by the first X-ray detector provides an indicia of a high Z material, for example if the image includes a spot that corresponds to an absorption of X-rays, the truck 120 is sent to the muon imaging station 110.

The muon imaging station 110 includes an upper detector unit 112, a lower detector unit 114, and a spectrometer 116. The detectors described herein are not limited to detecting muons; they can react to any charged energetic particle that passes through them. However, of all naturally occurring forms of radiation, only cosmic muons are likely to penetrate both detector units while interacting with the detectors. Any event in which a particle that is detected in the upper detector unit 112 and at least one particle is detected in the lower detector 114 is assumed to be due to a muon passing through both detector units.

The interactions between the muon and the material in the scanned volume 125 can yield additional charged particles that exit the scanned volume 125. The paths of these particles tend to be close to the muon, and hence the location of the muon can be usually determined with reasonable accuracy even in their presence. For example, by taking the average location of all the energies deposited in a detector layer to be the location of the muon. These additional particles are almost entirely electrons (and positrons), and are often stopped in the first layer of detectors.

Figure 2:
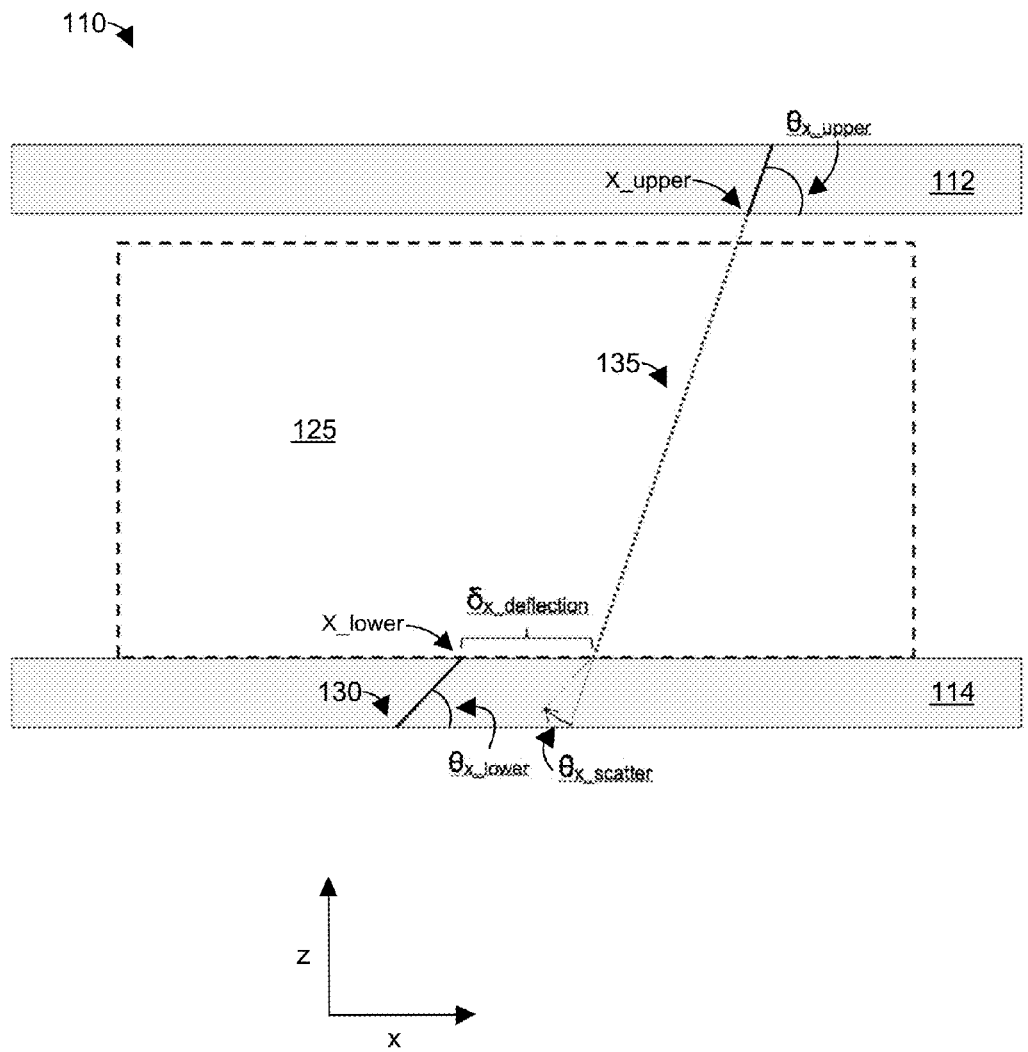
FIG. 2 is a block diagram that illustrates the scattering angle and deflection distance of a muon as it passes through a scanned volume.

The upper and lower detector units 112, 114 each include at least two detection layers for each of the two coordinates that define the muon's location as it passes through the detector plane. For example, labeling the vertical axis as z, a simple embodiment includes two detectors, each one measuring the x and the y coordinate of the detected muon. More generally, the axes of deflection, "x" and "y", refer to two orthogonal directions that are in the plane where the location of muons is measured after they transverse the scanned volume. The upper detector unit 112 can detect the location and direction in which a muon 130 travels through it. By this measurement, the upper detector unit 112 can determine the position and incidence angle of the muon 130 before entering the scanned volume 125, for example, a truck 120 or a shipping container. The lower detector unit 114 can also detect the location and direction of the muon 130 as it travels through it. By this measurement, the lower detector unit 114 can determine the exit angle of the muon 130 after exiting the scanned volume 125. The difference between the incidence angle and the exit angle is the scattering angle of the muon 130 due to the materials in the scanned volume 125 through which the muon 130 travelled. It is useful to separate the scattering into two angles, $\alpha_x$ which lies in the x-z plane and $\alpha_y$ which lies in the y-z plane. Furthermore, the paths measured at the upper detector 112 and lower detector 114 can be extended to the lower edge of the scanned volume 125, and the distance between them due to the deflection of the muon by the material in the scanned volume can be measured. Again, it is useful to separate the deflection distance into its x and y components, $\delta_x$ and $\delta_y$. FIG. 2 illustrates the scattering angle and deflection distance in the x-z plane. Such information can be useful to infer the type of material in the scanned volume 125 and, thus, whether high-Z material is present in the scanned volume 120.

The scanned volume 125 can include all of the volume between the upper and lower detector units 112, 114, or it can be defined to be a smaller volume, as illustrated by the dashed line in FIG. 2. The latter choice neglects any muon scattering that occurs between the detector units but outside the scanned volume, which can be useful when this additional volume is known to contain only air. For example, when scanning a cargo container its external dimensions and the scanned volume can be defined to exclude the air volume above the container.

After the muon 130 passes through the lower detector 114, the muon 130 enters the spectrometer 116. The spectrometer 116 includes a passive layer (e.g., a lead sheet, steel, and/or iron), a detector layer, and an air gap between the passive and detector layers. The spectrometer 116 can include one or more sets of passive layer-air gap-detector layer. The spectrometer 116 measures the muon energy, or equivalently, its absolute momentum p. In some embodiments, the passive layer in the spectrometer can be a commercially-available lead sheet (e.g., purity of 50-100%) or a lead-enriched steel sheet. The lead sheet or lead-enriched steel sheet can be placed on a supporting steel plate or a steel mesh.

Figure 3:
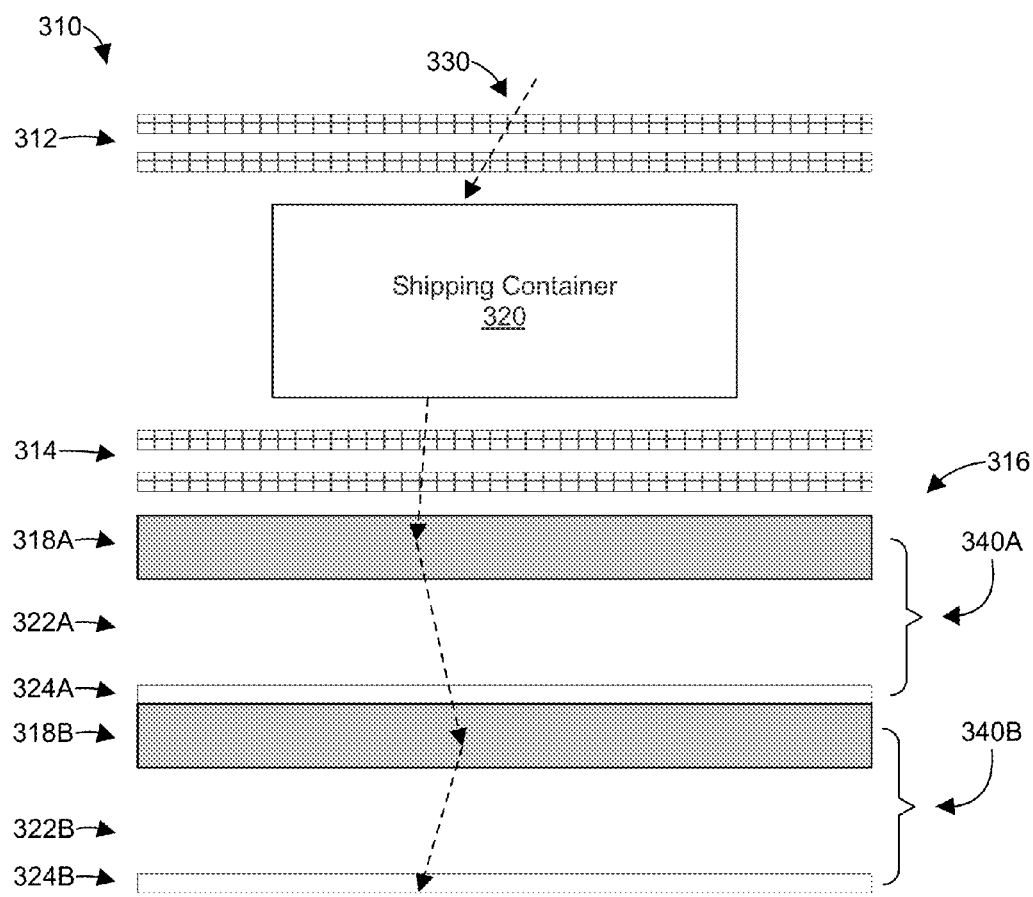
FIG. 3 is a block diagram of a typical muon imaging station.

FIG. 3 is a block diagram of a typical muon imaging station 310. As discussed above, the muon detector 310 includes an upper detector unit 312, a lower detector unit 314, and a spectrometer 36. The upper and lower detector units 312, 314 each include two layers of detectors that measure the location of the muon's passage in the x-y plane. The spectrometer 316 includes a first detector set 340A and a second detector set 340B. The first detector set 340A includes a passive layer 318A, an air gap 322A, and a detector layer 324A. Similarly, the second detector set 340B includes a passive layer 318B, an air gap 322B, and a detector layer 324B.

Figure 4:
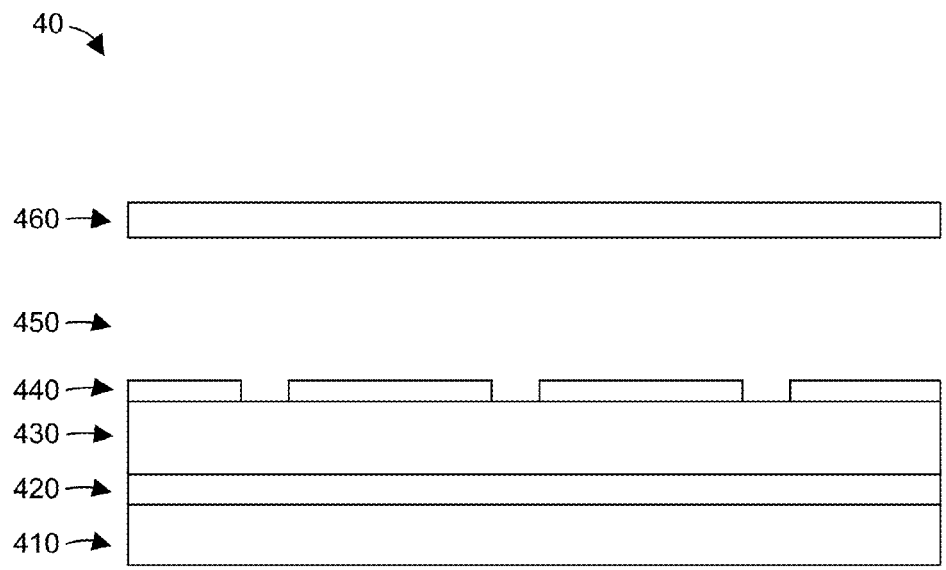
FIG. 4 is an example of a detector from a detector layer in a typical muon imaging station.

FIG. 4 is an example of a detector from a detector layer of detector units 312, 314. The detector 40 includes a plastic stage 410, a printed circuit board (PCB) 420, a resistive plate 430, a drilled board 440, a drift volume 450, and a cathode 460.

The plastic stage 410 is configured to be mounted on the circuit board 420. The plastic stage 410 receives an external force (e.g., from screws, bolts, a clamp, a mechanical assembly) to press the circuit board 420 towards the resistive plate 430 (or vice versa). In some embodiments, the plate 430 includes holes for receiving screws or bolts that are driven between the plastic stage 410 and the plate 430. The holes can be disposed along a perimeter of the stage 410 and/or on its interior surface. This mechanical force can create electrical contact between the circuit lines on the circuit board 420 and the resistive plate 430. This is an advantage over the prior art approach of adhering a circuit board to a resistive plate with conductive glue/epoxy. In addition, the plastic stage 410 can distribute the external mechanical force across the circuit board 420 to prevent bending or cracking of the circuit board 420 or damage to its electrical contacts. In some embodiments, alternative materials can be used to contrast the plastic stage 410. For example, the plastic stage 410 can be formed out of any rigid and insulating material, such as the epoxy substrates used for a printed circuit boards, a ceramic (e.g., alumina, berrylia, etc.) substrate, or similar materials.

The printed circuit board 420 is disposed between the plastic stage 410 and the resistive plate 430. The readout lines in the circuit board 420 face the resistive plate 430 and thus directly collect the charges produced in the gas for both the x and y coordinates. The PCB 420 can be manufactured using industry standard techniques.

The circuit board 420 includes circuit lines running along a surface of the circuit board 420 that faces the resistive plate 430. The circuit lines include first circuit lines for measuring a first coordinate (e.g., the "x" coordinate) and second circuit lines for measuring a second coordinate (e.g., the "y" coordinate). The first and second circuit lines can have various orientations with respect to each other. For example, the first and second circuit lines can be disposed orthogonally to each other (e.g., along the vertical and horizontal axes), at a 45-degree angle with respect to each other, a 30-degree angle with respect to each other, a 10-degree angle with respect to each other, or any other orientation. For example, some circuit lines can run parallel to the x axis of the circuit board 420 (horizontally in FIG. 1) to measure the y coordinate and some circuit lines can run parallel to the y axis (vertically in FIG. 4) to measure the x coordinate. The circuit lines that measure the x and y coordinates can be configured in a comb-like pattern. The circuit lines can be aligned with the holes in the drilled board 440.

The resistive plate 430 is disposed between the printed circuit board 420 and the drilled board 440. The resistive plate 430 can be made from a plastic polymer designed for electrostatic discharge. In some embodiments, the resistive plate 430 is between about 0.4 mm and 4 mm in thickness, for example about 0.4 mm, about 0.6 mm, or about 4 mm in thickness. In other embodiments, the thickness of plate 430 is greater than 4 mm, which can correspond to the thickness of readily available plates of such materials, such as SEMITRON® ESD 225 (available from Quadrant Plastics Composites Inc.).

The presence of the resistive plate 430 allows the detector to operate with large electric fields (e.g. 5 MV/m) without suffering from sparks. In particular, even cosmic muons that ionize many electrons, leading to larger electron showers, are unlikely to result in a spark. With these large electric fields, the detector can provide robust amplification with large gains (e.g., $10^4$-$10^6$). Large detectors generally require large gains since their readout strips have higher capacitance and thus require larger signal charges.

The drilled board 440 is a printed circuit board with a plurality of holes defined therein. The drilled board 440 can be a single-faced copper-clad printed circuit board having an epoxy substrate (e.g., FR-4). The copper thickness can be chosen according to industry standards, such as 17 microns or 35 microns. In some embodiments, the drilled board 440 is formed of multiple sub-units of identical drilled boards to provide a scalable configuration. For example, the drilled board 440 can be formed of a 4×4 array of modular drilled boards.

The cathode 460 is disposed above the drilled board 440, the space between the cathode 460 and the drilled board 440 defining the drift volume 450. The detector 40 is placed in a sealed volume filled with gas, filling the drift volume 450 and the holes in the drilled board 440. The gas can include Ar, Ne, and/or He. For example, the gas can be 90% Ar and 10% CO2, 30% Ar and 70% CO2, or 95% Ne and 5% CF4. The gas can have a pressure slightly above atmospheric pressure, e.g., 1.005-1.03 bar at sea level. The cathode 460 applies a voltage across the drift volume 450 to the drilled board 140. The voltage is chosen to yield a drift field of 0.1-1 kV/cm.

In operation, a charged particle (e.g., a muon) passing through the drift volume 450 ionizes the gas therein. The drift field in the drift volume 450 pushes the electrons towards the drilled board 440. The large field in the holes of the drilled board 440 guides the electrons into the holes where they create electron avalanches. The resulting charge flows through the resistive plate 430 and is conducted by the readout PCB 420 toward the readout electronics, which typically reside outside the gas volume.

Figure 5:
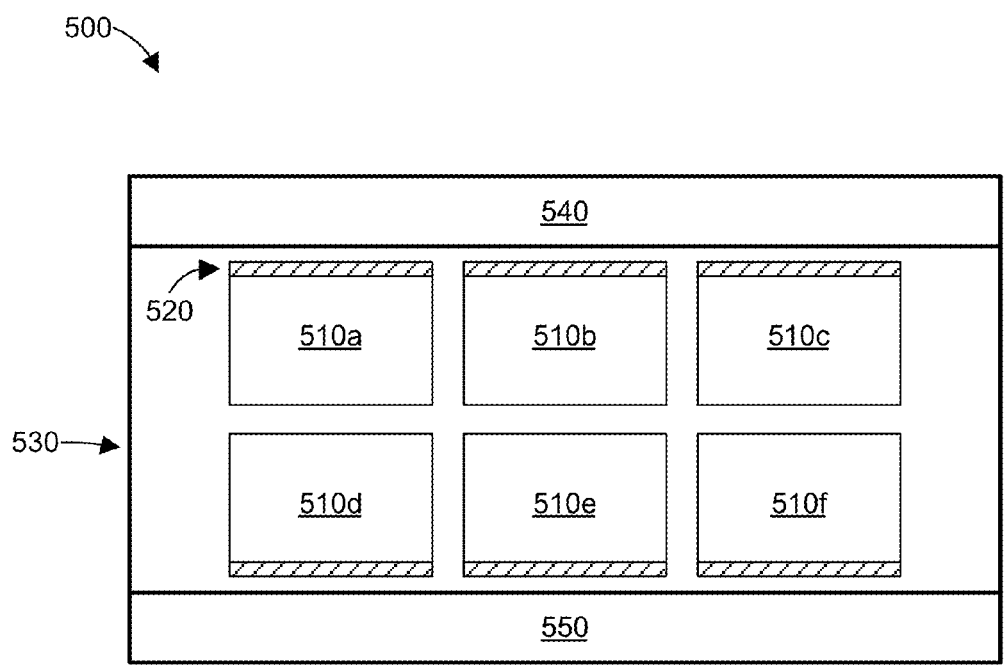
FIG. 5 is a block diagram of a detector layer in the form of a detector module for detecting charged particles.

FIG. 5 is a block diagram of a detector layer in the form of a detector module 500 for detecting charged particles. The module 500 includes an 3×2 array of detector units 510a, 510b, 510c, 510d, 810e, and 510f (generally detector units 510). The module 500 is scalable as fewer or additional detector units 510 can be included. The detector units 510 are the same or substantially the same as the detector unit 40 described above. Each detector unit 510 is configured to have an electronic readout 520 on a single edge of the respective detector unit 510. The electronic readouts 520 are connected to electronics boxes 540, 550. The electronics boxes 540, 550 each include a control panel, communications interfaces, front end units (FEUs), and one or more processors or field programmable gate arrays (FPGAs). The control panel can include controls for the DC voltage applied to the detector units and for gas flow to the module 500. The communications interfaces can include Ethernet ports, WiFi transceivers, or other communications interfaces to communicate with the detectors 510. The communications interfaces can also include a PC interface to connect to a computer, a server, etc.

The detector units 510 are disposed in a housing 530 that retains a gas. The gas can be an Ar-, Ne-, or He-based gas mixtures, for example ArCO2 (90%, 10%) or NeCF4 (95%, 5%). The housing 830 can be formed out of a metal or it can be lined with a metal.

Returning to FIG. 3, in operation a muon 330 passes through the upper detector unit 312 where each detector can measure the x and y coordinates of the muon 330. Using the pairs of (x, y) coordinates measured by the detectors in the upper detector unit 312 and the known height of the detectors, a control system can determine the incidence angle and location of the muon 330 before it enters a volume 320 to be inspected, such as a shipping container or a truck. The muon 330 then passes through the volume 320 where the trajectory of the muon 330 may change based on the contents of the volume 320. After the muon 330 exits the volume 320, the muon 330 passes through the lower detector unit 314 where each detector can measure the x and y coordinates of the muon 330. Using the pairs of (x, y) coordinates measured by the detectors in the lower detector unit 314 and the known height of the detectors, the control system can determine the exit angle and location of the muon 330 as it exits the volume 320.

Next, the muon 330 passes through the spectrometer 316, where its position can be detected at active layers 324A and 324B. The muon 330 can be deflected by the passive layers 318A, 318B. In some embodiments, a controller can model the path of the muon 330 as it travels between the passive layers 318A, 318B as a series of straight line segments. For example, the controller can model the path of the muon 330 from the lower detector unit 314 to passive layer 318A, from the passive layer 318A to the next passive layer 318B, and from passive layer 318B to active detector layer 324B as straight line segments (as illustrated in FIG. 3). The scattering angles of the muon 330 between these line segments can be used to measure the momentum of the muon 330, as muons with low p tend to scatter more.

The passive layer can contain lead, which can scatter the muons well due to its high scattering density λ. In particular, for the same weight, lead scatters muons over twice as much as steel does. In some embodiments, the passive layers contain commercially available lead sheets that are placed on a steel support plane. Thus the same scattering of muons is achieved with less weight, simplifying the mechanical support structure as a whole.

Furthermore, the material in the passive layers 318A, 318B may stop muons with low p. Thus when the measurements of the lower detector unit 214 indicate that a muon should have reached the detector layer 324, but no such muon was registered there, this indicates a muon of low p.

Figure 6:
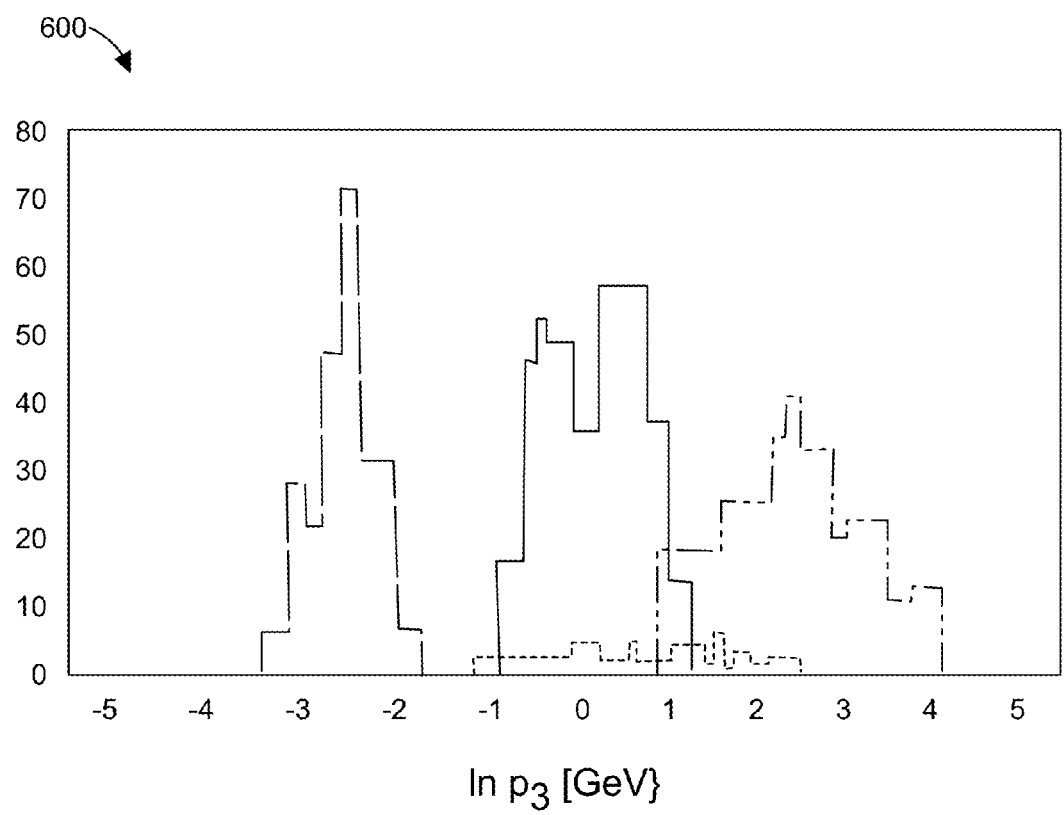
FIG. 6 is a graph to illustrate how muon scattering and absorption can be used in a spectrometer to measure muon momentum.
Figure 6:
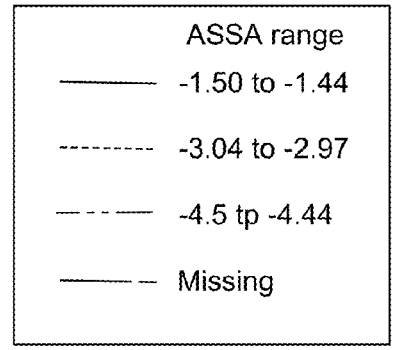

FIG. 6 is a graph 600 to illustrate how muon scattering and absorption can be used in the spectrometer 316 to measure p. In this simulation, cosmic muons pass through a loaded shipping container and then enter a spectrometer 316 with 1 cm thick lead sheets as its passive layers 218A, 218B. Muons that failed to reach either detection layer 324A, 324B in the spectrometer 316 are shown as "missing" in the graph 400. For muons that are detected in layers 324A and 324B, four scattering angles are measured: one in the x-z plane and one in the y-z plane for each layer of the spectrometer. We first scale each angle by $\sqrt{\cos\Theta}$, where $\Theta$ is the estimated (3D) zenith angle of the muon through the relevant passive layer. This accounts for the dependence of the scattering angle on the length of its path through the passive layer. We then average all four scaled scattering angles to find the Average Scaled Scattering Angle (ASSA). For each range of ASSA values we can find the corresponding distribution of p for the cosmic muons simulated to have ASSA values in that range. Three such ranges are shown in FIG. 4, demonstrating that large scattering angles indicate low p, and that missing muons indicate yet lower p.

Furthermore, muons with large p tend to produce more additional particles that can be detected in the top detector layer of the lower detector unit 214. When the distances between the muon and the additional particles are larger than the spatial resolution of the detectors, this can be identified as used to refine the measurements of p. For example, the measurements can be refined by conditioning the (simulated) a postpriori distributions of p not only on the ASSA and the missing hits but also on the number of distinct particles observed in the top detector layer of the lower detector unit 314. In some cases, even when the distances between the muon and the additional particles are small, their presence can be inferred from the width and spatial structure of the energy deposit in said detector, which may be inconsistent with those expected from a single particle with the observed incidence angle and location.

Figure 7:
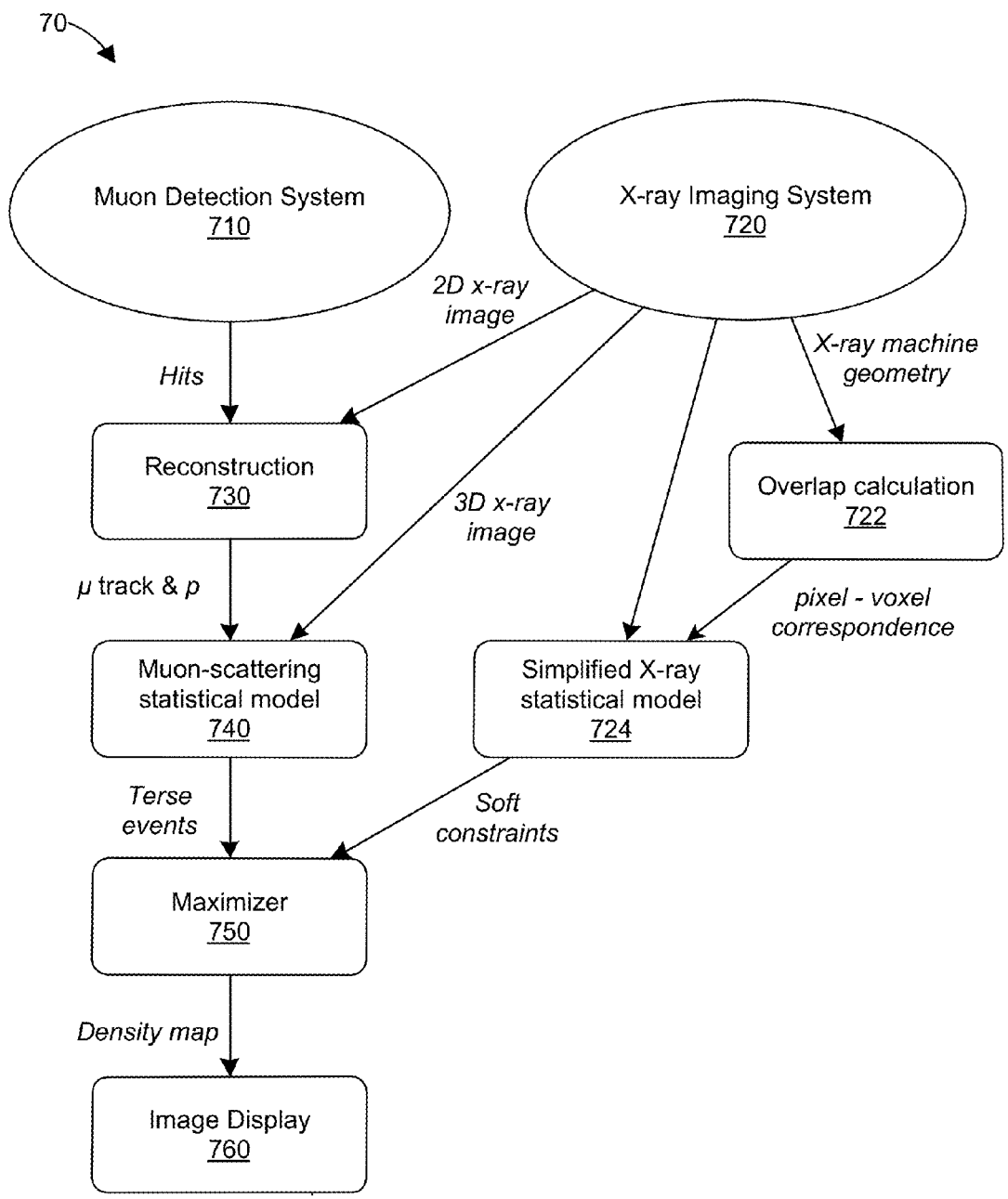
FIG. 7 is a flow chart of an embodiment for scanning a volume using information from a muon detection system and an X-ray imaging system.

FIG. 7 is a flow chart 70 of an embodiment of scanning a volume using information from a muon detection system 710 and an X-ray imaging system 720. In reconstruction step 730, the muon's momentum and the muon's track, that is, its location and direction when entering and exiting the scanned volume, are reconstructed using the detection signals (hits) from the muon detector system 710, as discussed below. In step 740, the muon statistical model summarizes the data from each muon scattering event, the detector performance, and the physical muon scattering model incorporated in the likelihood into a terse event description, as detailed below. The muon statistical model 740 can incorporate an a priori 3D mass density map (APMDM), which may be derived from the measurements of the X-ray imaging system 720, as detailed below.

Figure 8:
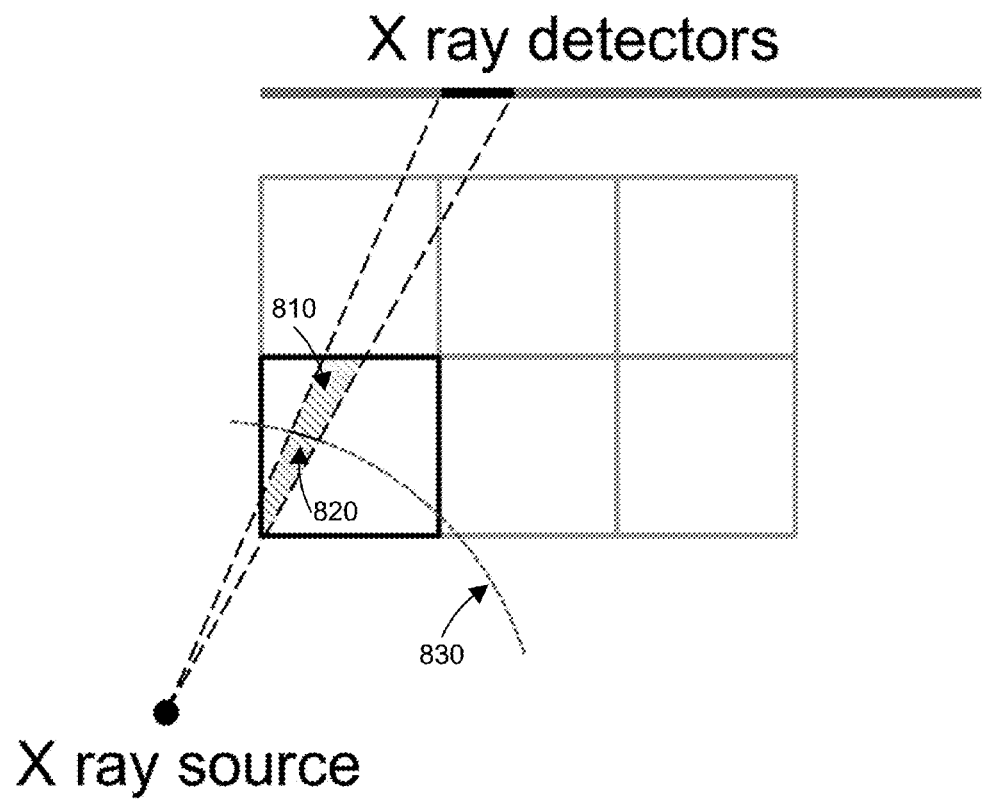
FIG. 8 is a diagram that illustrates the alignment of X-ray pixels and voxels along an axis.

In the overlap calculation step 722, the geometries of the muon measurement system 710 and the x-ray imaging system 720 are used to calculate the average path length within each voxel (from 710) for paths that end up in each pixel (from 720). A common scenario is that the X-ray pixels and the voxels are aligned along one axis. As illustrated in FIG. 8, the calculation in a plane perpendicular to that axis can be approximated as the area of the overlap 810 divided by the length of the arc 820 of the circle 830 centered on the X-ray source and limited to the overlap. In step 724, the simplified x-ray statistical model summarizes the implications of the x-ray image on the scattering density map into a list of soft constraints, as detailed below.

The maximizer step 750 determines the most likely scattering density map Λ, that is, the 3D map that maximizes the likelihood function L(Λ) described by the terse events and the soft constraints. The image display step 760 presents the operator with a visual representation of the scattering density map.

Figure 9:
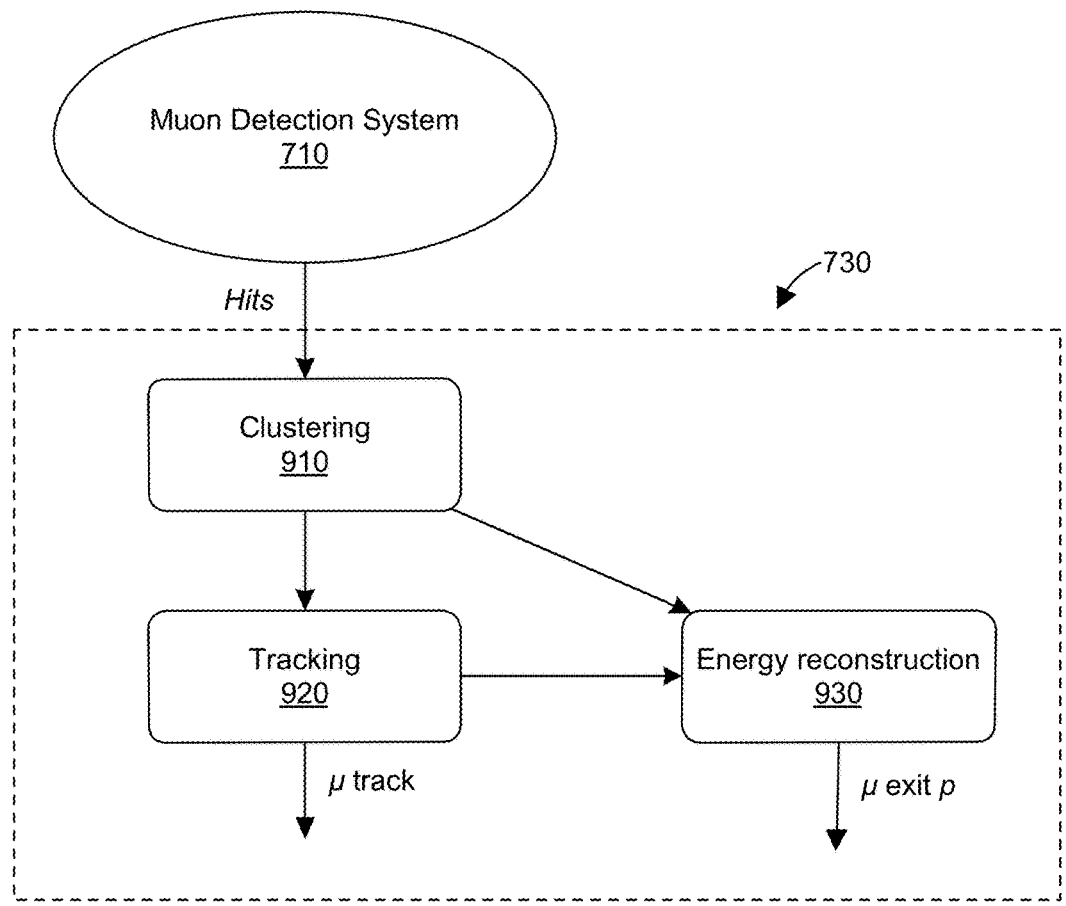
FIG. 9 is a flow chart of the reconstruction step from FIG. 7.

FIG. 9 is a flow chart of the reconstruction step 730 discussed above. In step 910, the hits from each detector layer are clustered to find the locations in which energetic charged particles passed through that layer. Often this is trivial as there is only one hit per coordinate per layer, and its location is the desired output. As those familiar in the art will appreciate, ambiguities may arise when several particles are detected. Some ambiguities can be resolved using auxiliary information, such as the size of the signals, and some through comparisons to the locations found in adjacent detector layers. When significant ambiguities remain, e.g., larger than 1 cm, the event can be discarded. In step 920, the muon paths before and after the scanned volume are reconstructed as straight-line segments between the measured locations. In step 930, the momentum with which the muon exited the scanned volume is estimated as discussed above, using any missing hits, the ASSA, the existence of multiple locations in the upper detector layer below the scanned volume, etc.

In another embodiment, the momentum estimation in step 930 combines the information measured in the spectrometer with the a-priori spectrum of cosmic muons. Furthermore, while low energy muons tend to arrive roughly from the zenith, the directions of incoming higher-energy muons are more uniform. This information can be used by conditioning the a priori spectrum on the incidence angle measured in step 920. The information can be combined using an analytical description of the measurement, e.g., as a Gaussian distribution, and the spectrum. The information can also be combined using simulated a postpriori distributions such as those in FIG. 6, which can be multiplied by the ratio of the desired a priori distribution and the a priori distribution that was used to generate the simulation.

Furthermore, data can be collected without a cargo present, and the a priori cosmic muon can be tuned to match that data and thus account for the local conditions at the site, such as latitude, height above sea level, and the quantity of the materials above the detection system.

When the measurements of the muon momentum below the scanned volume are combined with the a priori distribution, the expected energy loss can be taken into account. For example, the a postpriori momentum distribution can be calculated as $P(p_f=p|D)=P(p_i=\Delta+E(p)|\theta_i)P(p_f=p|S)$, where $p_f$ is the random variable whose value is the muon's momentum as it arrives at the spectrometer 116, p is a positive number, D is the measured data, $p_i$ is the random variable whose value is the muon's momentum at the entrance to the scanned volume 125, $\Delta$ is the expected energy loss, E(p) is the energy associated with this momentum, $\theta_i$ is the muon's incidence angle, and S is the measured spectrometry data.

Various statistics can be used to summarize the a postpriori momentum distribution into a single number which will be used as the muon's momentum p, for example, the median or mean. Another equally attractive option is to use the most likely value. However, since the width of the muon scattering distribution is inversely proportional to p, the scattering of muons reconstructed as having large p will be assigned more weight in the likelihood. There is no particular reason to assume that overestimating p and underestimating p are equally problematic. Thus, asymmetric statistics can improve the mapping of the scanned volume. For example, given the distribution $f(p)$, instead of the mean estimator $\hat{p}=\int p f(p)dp$ we can use $\hat{p}=Ep+N\sigma$, where $N\in \mathbb{R}$ and $\sigma$ is the standard deviation of $f(p)$.

Figure 10:
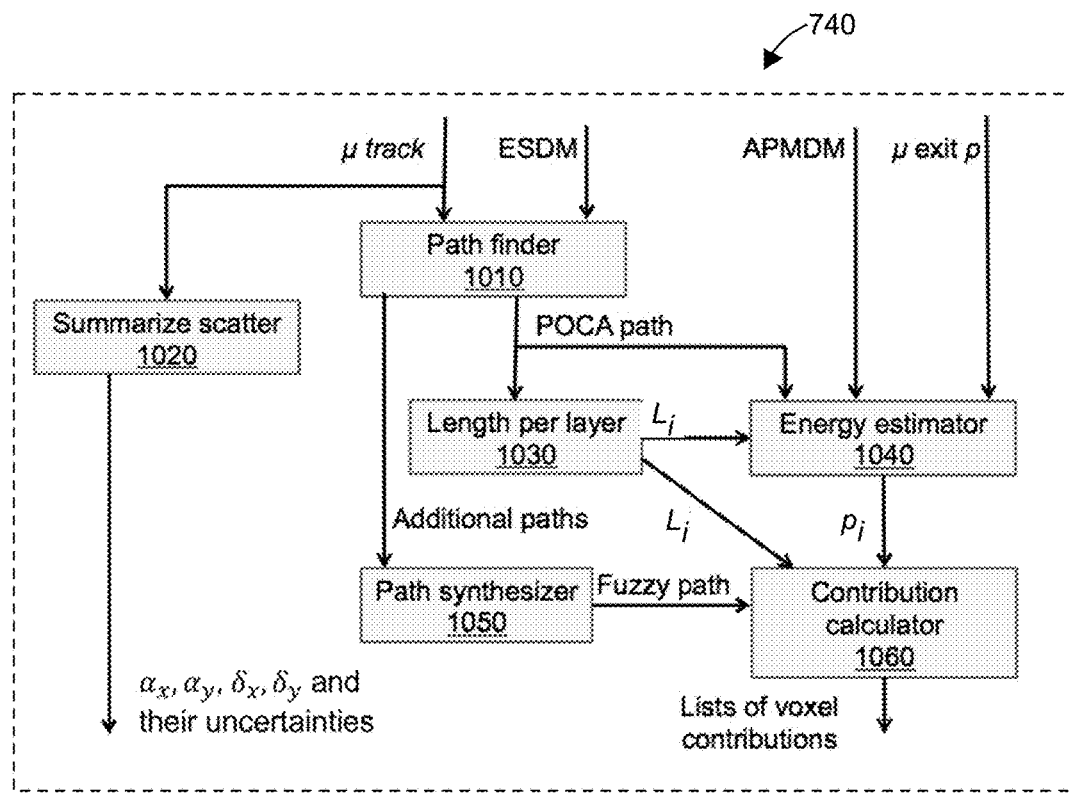
FIG. 10 is a flow chart of the muon-scattering statistical model step from FIG. 7.

FIG. 10 is a flow chart of the muon-scattering statistical model step 740 discussed above. The path finder module 1010 finds the nominal path of the muon through the cargo and additional paths of interest, as detailed below. The event-level observables, namely the scattering angles, the deflection distances and their measurement uncertainties are calculated in step 1020. The length of material through each layer of voxels is calculated in step 1030 as $$L_i = \frac{L_z}{\cos\Theta_i},$$

where $L_z$ is the height of the voxels, $\Theta_i$ is the 3D zenith angle of the muons in the i-th layer of voxels according to the POCA path, and $L_i$ is the length of the i-th layer of voxels. The estimated momentum of the muon at each layer is calculated in step 1040, as detailed below. The path synthesizer step 1050 can smear and combine paths and path segments to create one or more paths. Each path is a list of relevant voxels and their relative weights, $w_j$. The final step 1060 is to calculate the contribution of each voxel to the covariance matrices of the observables, as detailed below. The outputs of steps 1020 and 1060 make up the "terse event" summary for each muon.

When muon tomography is used in conjunction with X-ray imaging, an a priori 3D mass density map (APMDM) can be derived, by back projecting a previously taken X-ray image unto the scanned volume. An APMDM can also be estimated indirectly, e.g., from the declared content of the scanned volume using a database of mass densities, possibly using a lookup of similar cargoes in a database. The X-ray image can also be used to lookup similar cargoes in a database. The APMDM can be translated to an estimated scattering density map (ESDM). The APMDM and ESDM are not crucial to the functioning of the algorithm, as detailed below. On the other hand, even less-than-perfect APMDMs and ESDMs can improve the accuracy of the reconstruction.

Figure 11:
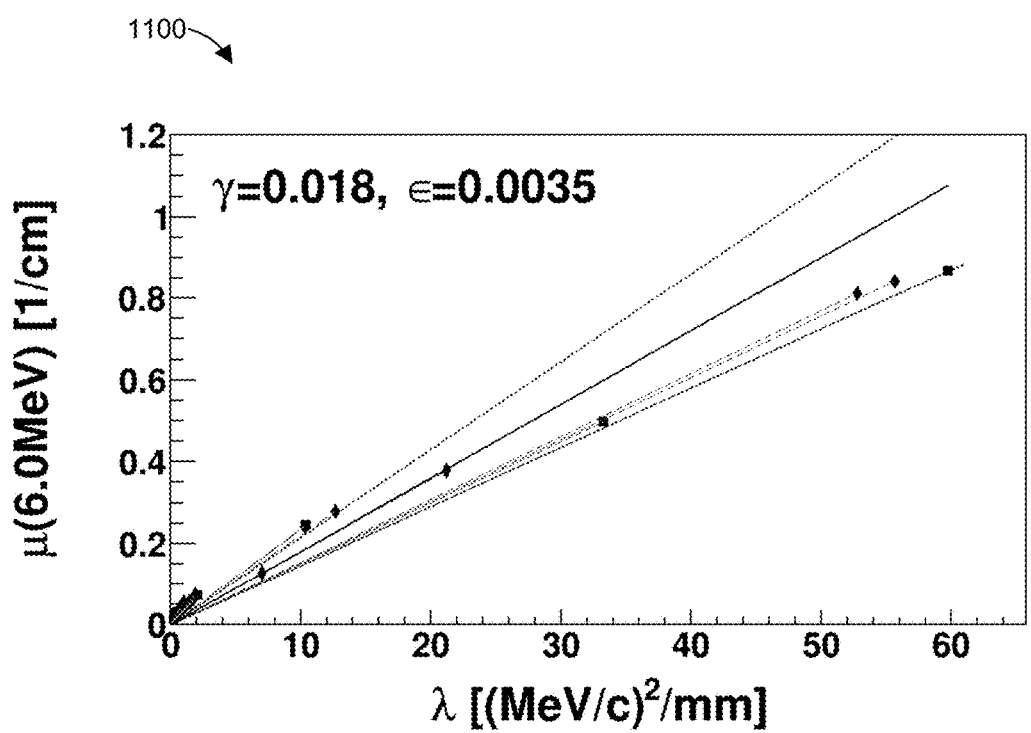
FIG. 11 is a graph of the scattering density from an x-ray-based a priori 3D mass density map (APMDM)

As an illustration of estimating the scattering density from an x-ray-based APMDM, FIG. 11 shows a graph 1100 of a simple linear estimate $\lambda=\mu/\gamma$ where $\mu$ is the X-ray attenuation coefficient, and $\gamma$ is a constant. The figure shows the $\lambda$ and $\mu$ values for selected solids and liquids relevant to cargoes such as glass, fibers, copper, iron and concrete (marked as diamonds) and for key materials for the detection of shielded high-Z contraband, such as plastics, steel, lead and Uranium (marked as squares). Since a voxel can contain varying amounts of air (or other light materials) in addition to these solids, any point along the gray lines connecting the origin with the values for these pure materials is also relevant. The importance of such mixed voxel content also motivates the choice of the simple linear approximation above.

Returning to FIG. 10, the path finder module 1010 finds the point of closest approach (POCA) between the incoming muon track and the outgoing muon track. The POCA path is then defined to include the straight-line segments between the entry point to the POCA and between the POCA and the exit point. Often the detectors extend beyond the edges of the cargo, so that the volume between the detectors is known to be empty outside of a well-defined region, and the scanned volume is defined to cover only a part of the region between the detectors. In this case, the entry and exit points can be redefined so that the incoming and outgoing tracks extend to the edges of the scanned volume, so that the POCA path can enter and exit the scanned volume from its sides. The POCA path is used as the nominal path of the muon through the cargo. The POCA path can be further modified to account for information from external sources, summarized in an ESDM. In particular, since the total weight of a shipping container or truck is often limited, dense cargo is usually packed at the bottom of the cargo with only air above it. When these scenarios are identified in the ESDM, the POCA can be replaced by the nearest point below the maximal height of the solid cargo. More generally the POCA can be constrained to the set of voxels identified as having an ESDM above some threshold.

The path finder module 1010 also identifies other paths of interest, such as paths were the sharp turn of the POCA path is replaced with two or more gradual turns. Such paths can be constructed taking the ESDM into account, as turns are more likely where the scattering density is high. Alternatively, path finding can be performed iteratively in tandem with the maximization, and the paths can be constructed taking the current scattering density map ($\Lambda_n$, defined below) into account. Furthermore, when paths are refined iteratively, they can be combined using so called "genetic" algorithms, e.g., by combining their turning points.

The path finder module 1010 also identifies path segments of interest, such as the line segment that continues the muon's entry track down to the height of the POCA and the line segment that continues the muon's exit track up to that height.

The energy estimator module 1040, estimates the magnitude of the momentum (which is equivalent to estimating the energy) in each layer of voxels. The energy loss in the i-th layer is estimated as $\Delta E_i = P_s \rho L_i$, where the stopping power $P_s$ can simply be approximated to 1.6 MeV $g^{-1}$ $cm^2$. The mass density $\rho$ can be taken from an APMDM using the location estimated nominal (POCA) path, or from a simpler 1D APMDM that depends only on i, or a simple constant can be used, e.g., $\rho=1$ g $cm^{-3}$ Starting with the lowest layer of voxels, were the muon's momentum at the exit was reconstructed, the energy losses are translated into momentum losses, and the momentum at the entry is calculated for each layer. The momentum in the i-th layer, $p_i$, can then be taken to be the average of the entry and exit momenta.

In another embodiment (which extends the flow shown in FIGS. 7, 9 and 10), the energy reconstruction step 730 is delayed until the total energy loss along the POCA path, $\Delta$, is estimated in the energy estimator module 1040. This estimate can then be used when combining the a priori spectrum with the spectrometer measurements, as described above.

The path synthesizer module 1050 translates each of the geometrical paths suggested by the path finder module 1010 into a list of voxels, each with its own weight. The simplest choice is to assign one voxel per layer, such as the voxel that includes the mid-height point of the path, yielding an ordered list of voxels that belong to the path (though this order plays no role in the calculations that follow). Other assignments include more than one voxel per layer, resulting in a "fuzzy path," where the path of the muon is defined less precisely and more voxels contribute their scattering densities $\lambda_j$. As an example, we can calculate the length of the path in each voxel and weight the voxels in each layer according to these lengths, so that the total weight of the voxels from each layer equals one. Another example is to combine path segments, allowing voxels from several paths segments to contribute to the same layer. In particular, the path synthesizer can combine the POCA path with the path segments that continue the entry and exit tracks, and the relative weight of these contributions can vary from layer to layer. One choice is that in the i-th layer the weight of the POCA path is $$1 - \frac{z_0 - z_i}{z_0 - z_p}$$

above the POCA and $$1 - \frac{z_i - z_1}{z_p - z_1}$$

below it, where $z_0$, $z_1$, $z_p$, and $z_i$ are the heights of the top of the scanned volume, its bottom, the POCA, and the layer (respectively). Furthermore, the path synthesizer can smear the paths, e.g., according to a Gaussian resolution. The relevant smearing resolution can depend on geometric factors such as $z_0-z_i$ and $z_i-z_1$, on $p_i$, on the distance of closest approach, etc. In particular, the smearing can have a preferred direction, such as the direction between the POCA path and the path that extends the muon's entry track. We use the term fuzzy path to refer to paths that may include more than one voxel per layer. Finally, the path synthesizer combines all the relevant paths into a single fuzzy path. Each path receives its own weight, $W_l$, where l is the index of the path, so that $\Sigma W_l = 1$. The weight of the j-th voxel is then $w_j = \Sigma W_l w_{jl}$, where $w_{jl}$ is the weight of the j-th voxel in the l-th path.

The contribution calculator step 1060 calculates the contribution of each voxel in the fuzzy path to the covariance matrices of the scattering observables. There are two such matrices, one for $\alpha_x$ and $\delta_x$, and one for $\alpha_y$ and $\delta_y$. Given the j-th voxel in the i-th layer, the contribution of the m-th muon for the covariance matrix of the xz plane is $C_{jm} = w_j \lambda_j N_{jm}$, where $$N_{jm} = \frac{L_z}{B_{im}^2 \cos\Theta_{im}} \begin{pmatrix} 1 & f_x\left(T_i + \frac{1}{2}q_{im}\right) \\ f_x\left(T_i + \frac{1}{2}q_{im}\right) & T_i^2 + T_i q_{im} + \frac{1}{3}q_{im}^2 \end{pmatrix},$$

where $B_{im}$ is the kinematic term ($B=\beta p$) based on the momentum of the m-th muon in the i-th layer, $p_{im}$, $\Theta_{im}$ is the relevant 3D zenith angle, $f_x$ is a tunable parameter with a nominal value of 1, $T_i$ is the height difference between the bottom of the voxel layer and the bottom of the scanned volume, and $$q_{im} = \frac{L_z}{\cos^2\theta_{jm}},$$

where $\theta_{jm}$ is the appropriate 2D zenith angle (here, in the xz plane). This covariance matrix includes the standard expressions for the (approximate) scatter of muons through a layer of material, corrections due to the zenith angles of the muon, and the parameter $f_x$. The main use of $f_x$ is to reduce the correlations, as suggested by simulations of scatter through thick layers of dense cargo.

Returning to FIG. 7, the simplified X-ray statistical model step 724 is based on approximate relationships between the X-ray image and the per-voxel X-ray attenuation coefficients, and between X-ray attenuation coefficients and muon scattering densities. Each pixel of the X-ray image records the intensity of X-rays that reached it, $I_k$, where k is the index of the pixel. This can be related to the sum of the attenuation coefficients of the voxels along its path. A simple approximation is to treat the X-ray beam as monochromatic and to treat each voxel as having uniform content, yielding $-\ln$ $$\frac{I_k}{I_0} = \sum_{j=1}^{N_k} w_{k,j}\mu_j,$$

where $I_0$ is the initial beam intensity, $N_k$ is the number of voxels along the path from the X-ray source to the k-th pixel, $w_{kj}$ is the voxel-pixel overlap calculated in step 722, and $\mu_j$ is the attenuation coefficient in the j-th voxel. In this simple approximation we define $$D_k^X = -\ln\frac{I_k}{I_0}.$$

We then define a hidden variable, in the sense used in the EM algorithm, which quantifies the contribution of the j-th voxel to the k-th pixel, $G_{kj}$, and has the Gaussian distribution of $G_{kj} \sim G(\gamma\lambda_j, \epsilon\lambda_j)$, where $\gamma$ and $\epsilon$ are positive constants. We also define a hidden variable that describes the uncertainties on the k-th sum, $G_k^E \sim G(0, \sqrt{V_k^E})$, where $V_k^E$ includes the variance due to the measurement errors on $I_k$. We then impose (as detailed below) the "soft" constraints $D_k^X = g_k^E + \sum_{j=1}^{N_k} w_{kj} g_{kj}$, where $g_k^E$ is the value taken by $G_k^E$ and the $g_{kj}$ are the values taken by the $G_{kj}$ variables. This particular form was chosen because it leads to an EM algorithm whose maximization step is solvable analytically and quickly for several regularization schemes (as detailed below).

We choose $\gamma$ and $\epsilon$ values which describe the approximate relationship between X-ray attenuation and muon scattering densities. FIG. 11 illustrates such a choice, with the solid black line showing the expected slope $\gamma$, and the dashed lines showing the slopes $\gamma\pm\epsilon$. In some X-ray imaging machines the X-ray spectra varies from pixel to pixel, and the values of $\gamma$ and $\epsilon$ can be functions of the location of the pixel.

The attenuation of a wide-spectrum X-ray beam is more complicated, as the high energy components penetrate deeper than the softer components. Hence, even in the approximation that each voxel has uniform content, the attenuation of a wide-spectrum X-ray beam after two voxels is not the product of its attenuations for each of these two voxels. To (partially) model this effect, we can replace the $D_k^X$ defined above with more general functions of $$\frac{I_k}{I_0}.$$

This function can be tuned to best match calibration data collected with typical dense cargo and a long exposure period (e.g. 1 day), so that the muon scattering density map is determined with good precision.

For accurate reconstruction with long exposure, the muon statistical model can be extended to account for the non-Gaussian tails in the distributions of muon scattering (both in $\alpha$ and in $\delta$). For example, the contribution of the j-th voxel to the angular scattering can be modeled as a sum of several Gaussian distributions, all centered around zero. Even for exposures measured in days, a model including 4-6 Gaussians suffices for high-Z materials, and small biases for low-Z materials can be neglected. An optimization transfer algorithm can then be used to simplify the muon-scattering part of the statistical inference problem to one appropriate for an EM algorithm. Furthermore, the choice of the $$D_k^X\left(\frac{I_k}{I_0}\right)$$

functions can depend on the location of the X-ray pixel, to account for the spatial dependence of the X-ray spectrum.

The size of the X-ray pixels may be much smaller than the size of the voxels used in the muon scattering map. In such a case, there may be several X-ray pixels that have the same set of $w_{kj}$s. The model presented so far can account for discrepancies between the values of these pixels, treating them as statistical fluctuations in the $\mu$-$\lambda$ correspondence, as covered by the $\epsilon$ parameter. However, in practice such discrepancies are more likely to be due to uneven cargo content within the relevant voxels. The model can be improved (and its execution times reduced) by combining these constraints into a single constraint. The central value of this constrain is the average value of the per-pixel constraints, $$<D^X> = \frac{\sum D_i^X}{N_s},$$

where the index i enumerates the pixels that share the same set of $w_{kj}$s and $N_s$ is the number of such pixels. The variance for this constrain (the $V_k^E$) can then be increased to account for the indicated spatial non uniformity, e.g., by including a term of $$h\frac{\sum(D_i^X - <D^X>)^2}{N_s - 1},$$

where $0<h<1$.

Furthermore, the above treatment implicitly neglects correlations between the X-ray attenuations in various voxels. Such correlations can be large when only some of the X-ray beams that end up in a pixel pass through dense cargo. This can bias the intensities predicted by the statistical model upward. The presence of such correlations can be inferred from a large variance in the intensities measured in the neighborhood of the pixel, and a correction can be applied to $v_i$ of the form $-BR_i$, where $B>0$ and $R_i$ is an estimate of the local changes in the $D_i^X$ values near the i-th pixel. For example, the RMS of the nine $D_i^X$ values of the pixel itself and its eight nearest neighbors.

The maximizer step 750 finds the scattering map Λ that maximizes the likelihood L(Λ|D)=L_D(Λ|D)L_R(Λ), where D is the observed data (muon scattering observables and the X-ray image, if available), $L_D$ is the unregularized likelihood, also known as the data terms, and $L_R$ the regularization terms. Equivalently, the maximizer step 740 minimizes the minus log likelihood (MLL) M=−ln L=M_D(Λ|D)+M_R(Λ). Dropping any terms independent of Λ, the data terms are:

$$2M_D = \sum_m \ln|C_m^x| + \ln|C_m^y| + D_m^x(C_m^x)^{-1}(D_m^x)^T +$$

$$D_m^y(C_m^y)^{-1}(D_m^y)^T + \sum_k \ln V_k + \frac{(D_k^X - E_k^X)^2}{V_k},$$

where $C_m^x$ and $D_m^x$ are the covariance matrix and data for the "x" direction of scatter of the m-th muon, $C_m^y$ and $D_m^y$ the same for the "y" direction, $E_k^X$ and $V_k$ are the mean and variance of the k-th X-ray datum $D_k^X$ (as defined above). Furthermore, $C_m^x = C_m^E + \Sigma_j C_{jm}$ where $C_m^E$ is the covariance matrix describing the measurement errors on $$D_m^x = \begin{pmatrix} \alpha_{x,m} \\ \delta_{x,m} \end{pmatrix},$$

$C_m^y$ and $D_m^y$ are similar for the "y" direction, $E_k^X = \gamma \Sigma_k w_{kj} \lambda_j$ and $V_k = V_k^E + \epsilon^2 \Sigma_k w_{kj}^2 \lambda_j^2$. The regularization terms can be of the form $M_R(\Lambda) = \tau \Sigma_j (\lambda_j)^\kappa$, where τ≥0 is the regularization strength parameter and κ>0 is the regularization shape parameter.

Though prior art used 2≥κ≥1, and argued against κ<1, we find κ<1 to be particularly useful as it tends to bunch up the scattering density along the vertical axis, fighting a natural tendency of muon imaging to smear the images in this direction. On the other hand, regularization with κ>1 can exacerbate this unwanted smearing.

The maximizer step 750 performs an iterative algorithm, for example, an EM algorithm derived with the following hidden variables: $H_{jm}^x$ is a two component vector describing the contribution of the scatter in the j-th voxel to $D_m^x$, $H_m^{xE}$ is a two component vector describing the contribution of the measurement errors to $D_m^x$, $H_{jm}^y$ and $H_m^{yE}$ are similar contributions to $D_m^y$, $G_{kj}$ and $G_k^E$ (defined above) are contributions to $D_k^X$. The so-called "EM algorithm" can then be followed to produce the update equations of the scattering map. When a fuller description of the tails of the muon scattering distribution is needed, more complicated distributions can be used for $H_{jm}^x$ and $H_{jm}^y$, and other optimization transfers can be used instead of the simple EM algorithm.

Without the $D_k^X$ terms, e.g., when the X-ray image is not used, the resulting update equations can be separated so that $\lambda_{j,n+1}$, the scattering density of the j-th voxel in the n+1-th iteration, is the solution of an equation in λ of the form $$F_0(D, \Lambda_n) = \lambda + \frac{\tau\kappa}{2M_j}\lambda^{\kappa+1},$$

where $\Lambda_n$ is the scattering map after the n-th iteration and $M_j$ is the number of muon paths in which the j-th voxel appears.

In general, this equation cannot be solved analytically. However, the right-hand-side is a monotonously rising function of λ, hence a unique solution exists. We define a family $\mathbb{R} \to \mathbb{R}$ functions with parameter: $f_\eta^i(x)=x(1+\eta x^\kappa)$, and $f_\eta^s(x)$ as their inverse functions. The function $f_\eta^s(x)$ are known in the literature as "shrinking functions" since $f_\eta^s(x)<x$. The update can then be written as $\lambda_{j,n+1}=f_{\eta_j}^s(F_0(D,\Lambda_n))$, where $$\eta_j = \frac{\tau\kappa}{2M_j}.$$

In typical applications, $M_j$ and hence $\eta_j$ take one of only a few hundred unique values. We approximate each $f_\eta^s$ using cubic Hermite splines (CHS). The spline coefficients are readily calculable from $f_\eta^i(x)$ and its derivative. Using CHS is significantly more accurate and requires less computer memory than using a linear extrapolation. For example, in our tests even when allowing the linear extrapolation to use 10 times more intervals, the CHS were at least 20 times more accurate.

Without the $D_k^X$ terms, the resulting equation is in general not solvable analytically. However, there are a few useful exceptions. The first is when τ=0, that is, without regularization. In that case, the update equation is a simple quadratic equation with exactly one positive solution, which is used as $\lambda_{j,n+1}$. The second exception is when κ=1. In that case the update equation is a cubic equation with exactly one positive solution, which is used as $\lambda_{j,n+1}$. Furthermore, this positive solution is a continuous function of the coefficients of the cubic equation, and hence of $\Lambda_n$. Similarly, κ=2 leads to analytically solvable quartic equations.

In some embodiments, the maximizer step 750 interspaces the iterative steps based on the EM algorithms described above with quasi-Newton (QN) steps. A particular embodiment is detailed here. We define $\Delta_n=\Lambda_n-\Lambda_{n-1}$, for n>1, which is treated here as an abstract 1D column vector. We use at least 3 EM update steps before attempting the first QN step, and at least 2 EM update steps before each QN step. To find $\Lambda_n$ with a QN step, we proceed as follows. We set $u_0$, to be either the u used in the previous QN step, or if this is the first QN step, to be $\Delta_{n-3}$. We set $v_0$, to be either the v used in the previous QN step, or if this is the first QN step, to be $\Delta_{n-2}$. We set u=$\Delta_{n-2}$ and v=$\Delta_{n-1}$. We define the matrices U=(u_0 v_0) and V=(u v). We calculate the 2-by-2 matrix $A=U^T(U-V)$, and examine its determinant. If the determinant is zero, within computational tolerance, we declare the QN step a failure and try at least two more EM steps before the next QN step. If the determinant is non-zero, we find the correction vector $c=VA^{-1}U^Tu$. If L($\Lambda_{n-1}$+c)>L($\Lambda_{n-1}$), we take $\Lambda_n=\Lambda_{n-1}$+c. If not, but $$\left(\Lambda_{n-1} + \frac{1}{2}c\right) > L(\Lambda_{n-1}),$$

we take $$\Lambda_n = \Lambda_{n-1} + \frac{1}{2}c.$$

It not, we declare the QN step a failure and try at least two more EM steps before the next QN step.

Figure 12:
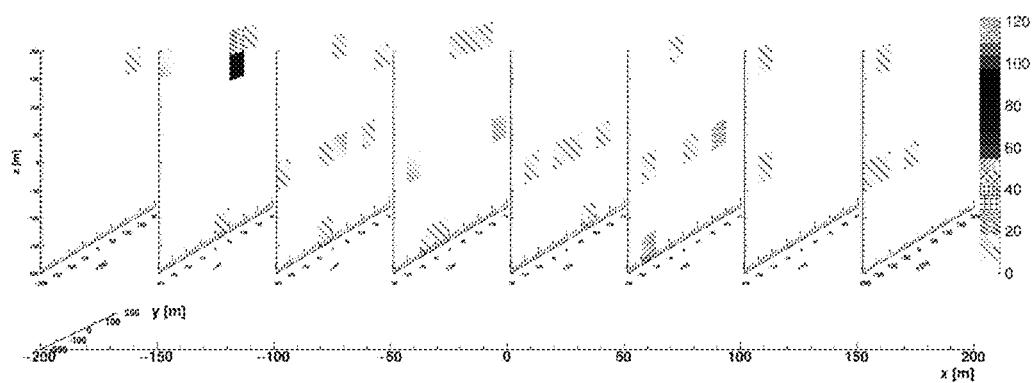
FIG. 12 is a graph of the relationship between X-ray attenuation and muon scattering densities.

The image display 760 can display the final scattering map, or if desired, previous maps. However, when regularization is used, the individual $\lambda_j$ values lack a clear physical interpretation. Hence the image display can also be "unshrunk" by applying the relevant $f_n^i(x)$ function to each $\lambda_j$ value. This recovers the physical values, e.g., a voxel filled entirely with aluminum would average a scattering density of 2.1, one filled with lead would average 33, and one filled with uranium would average 60. In one embodiment, useful for heavy cargo and shown in FIG. 12, the 3D map is illustrated in cross section along the y plane, and the scattering density of each voxel is visualized by hue and light intensity. The light intensity can increase monotonously and/or the hue can vary with the scattering density. Of course, the 3D map can be visualized in cross sections along the x or y planes as desired. In FIG. 12, the hues are suppressed and light grays are replaced with shadings, as detailed in the legend on right of the figure.

Figure 13:
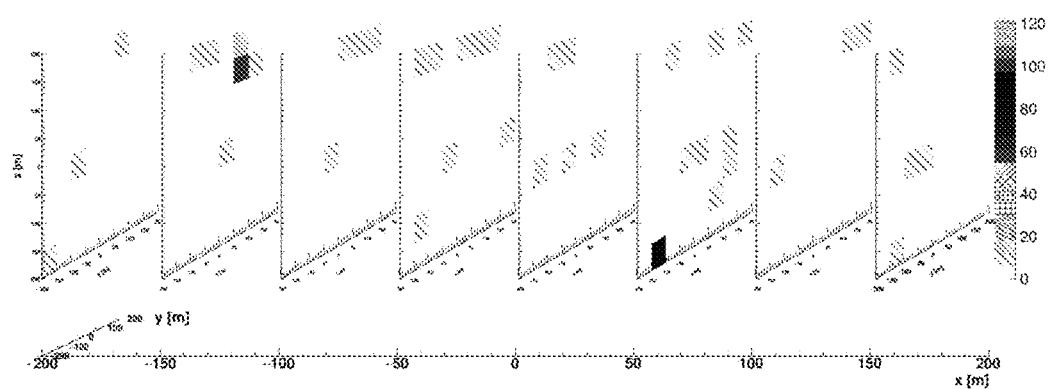
FIG. 13 is a visual representation of cross sections of a 3D scattering density map.

FIGS. 12 and 13 illustrate the gain from using the X-ray-derived constraints, as FIG. 12 shows a density map derived purely from muon scattering information while FIG. 13 shows a density map derived from the same muon scattering information supplemented with a 2D X-ray image. The muon scattering information is simulated for a 2 minute exposure, chosen to challenge the muon-only imaging, for a simulated $(40 \text{ cm})^3$ aluminum block, in which are embedded two $(5 \text{ cm})^3$ blocks of uranium (whose locations are reconstructed correctly in these images). The signal-over-background improves from 2.2 in FIG. 12 (muon only) to 6.7 with the 2D X-ray image in FIG. 13.

In some embodiment, a micro-processor based controller can analyze the final scattering map and set an alarm if it appears that a high-z material is present in the scanned volume. The alarm can be an audible signal, a visual signal, or a communication (e.g., a text message, email, phone call, etc.) to an inspector.

The present invention should not be considered limited to the particular embodiments described above, but rather should be understood to cover all aspects of the invention as fairly set out in the present claims. Various modifications, equivalent processes, as well as numerous structures to which the present invention may be applicable, will be readily apparent to those skilled in the art to which the present invention is directed upon review of the present disclosure. The claims are intended to cover such modifications.

What is claimed is:

1. A method of detecting a high atomic number (high-Z) material in a volume, comprising:
    placing a material in a volume to be scanned;
    scanning the volume, including the material, with an X-ray imaging system to detect the presence of dense material and to provide X-ray imaging data indicative of said presence of dense material;
    scanning the volume with a muon detection system to provide detection signals corresponding to muon scan data;
    using the muon scan data, reconstructing an exit momentum and incoming and outgoing tracks of muons that pass through the muon detection system, the incoming track including a first position and first direction of travel of the muons before the muons enter the volume, the outgoing track including a second position and a second direction of travel of the muons after the muons exit the volume, the exit momentum reconstructed for the muons after the muons exit the volume;
    calculating a muon-scattering statistical model using (a) the muon exit momentum and (b) the incoming and outgoing tracks of the muon;
    calculating from the X-ray imaging data an X-ray statistical model suitable for use in conjunction with the muon-scattering statistical model;
    determining a most likely scattering density map according to the muon-scattering and X-ray statistical models; and
    on a visual image display configured to show a scattering density map, displaying a visual representation of the most likely scattering density map of said material in said volume.

2. The method of claim 1, wherein the muon scan data is collected by a detector that amplifies ionization charges in electron avalanches that take place in a gaseous or liquid medium.

3. The method of claim 1, wherein the muon scan data is collected by a detector that amplifies the ionization charges in electron avalanches that take place in a gas that is at least partially confined in holes drilled into a printed circuit board.

4. The method of claim 1, wherein reconstructing the exit momentum and the incoming and outgoing tracks includes:
    clustering muon detector hits from each of a plurality of detector layers of said muon detection system to form clustered location data;
    determining a muon location in each detector layer based on the clustered location data;
    estimating the incoming track as a first straight line that passes through a first muon location in a first detector layer and a second muon location in a second detector layer, the first and second detector layers disposed above the volume;
    estimating the outgoing track as a second straight line that passes through a third muon location in a third detector layer and a fourth muon location in a fourth detector layer, the third and fourth detector layers disposed below the volume; and
    determining the exit momentum using (a) scattering angles of the muons in a spectrometer and (b) an absorption of muons in the spectrometer, the spectrometer disposed beneath the fourth detector layer.

5. The method of claim 4, wherein the exit momentum is further determined using (a) a number of distinct detector hits from the third or fourth detector layer or (b) a width and a spatial structure of an energy deposited in the muon detector hits in the third or fourth detector layer.

6. The method of claim 4, wherein an a postpriori distribution of the exit momentum of the muons is summarized into a nominal value using a biased estimator suitable for mapping a most likely scattering density of the muons.

7. The method of claim 4, wherein the spectrometer includes a lead enriched passive layer.

8. The method of claim 7, where the lead enriched passive layer includes a commercial grade lead sheet.

9. The method of claim 1, wherein the exit momentum is determined using an average of scaled scattering angles of the muons in a spectrometer, the spectrometer disposed beneath the scanned volume.

10. The method of claim 1, wherein the exit momentum is determined by modeling a path of each muon between adjacent passive layers in a spectrometer as a straight line, the spectrometer disposed beneath the scanned volume.

11. The method of claim 1, wherein the exit momentum is determined by conditioning an a priori momentum spectrum on an incidence angle of the outgoing track of the muon and accounting for an estimated energy loss due to a material disposed above a spectrometer, the spectrometer disposed beneath the scanned volume.

12. The method of claim 11, wherein (a) a distribution of the a priori momentum or (b) the outgoing track is calibrated using data collected by a same apparatus used to collect the muon scan data.

13. The method of claim 11, wherein the estimated energy loss is calculated along a path estimated for the muon using an estimated scattering density map (ESDM).

14. The method of claim 1, wherein calculating the muon-scattering statistical model includes using an a priori mass density map (APMDM) derived from the X-ray imaging data or a cargo manifest.

15. The method of claim 1, wherein calculating the muon-scattering statistical model includes using an estimated scattering density map (ESDM) derived from the X-ray imaging data, cargo manifests, or an a priori mass density map (APMDM).

16. The method of claim 1, wherein calculating the muon-scattering statistical model includes, for each axis of muon deflection in the volume:
    calculating a scattering angle between the incoming track and the outgoing track of the muon;
    calculating a deflection distance of the muon;
    determining a respective uncertainty of the scattering angle and the deflection distance; and
    calculating a contribution of each voxel to the scattering angle and the deflection distance.

17. The method of claim 16, wherein calculating the muon-scattering statistical model further includes determining a point of closest approach (POCA) between the incoming track and the outgoing track of the muon.

18. The method of claim 17, further comprising determining a muon path (a) from a first detector layer disposed above the scanned volume to a first edge of the scanned volume, (b) from the first edge of the scanned volume to the POCA, (c) from the POCA to a second edge of the scanned volume, and (d) from the second edge of the scanned volume to a second detector layer disposed below the scanned volume.

19. The method of claim 18, wherein calculating the muon-scattering statistical model further includes using an estimated scattering density map (ESDM) to refine the determination of the POCA and the muon path by locating each turn in the muon path in a high scattering density region of the scanned volume.

20. The method of claim 18, wherein calculating the muon-scattering statistical model further includes using an a priori 3D mass density map (APMDM) to estimate a momentum of the muon at each layer of voxels.

21. The method of claim 16, wherein calculating the muon-scattering statistical model further includes:
    determining alternative paths and/or path segments of the muon through the volume; and
    synthesizing the alternative paths into a fuzzy path of the muon, that includes at least one voxel per layer of voxels, and where each voxel includes a respective weight.

22. The method of claim 16, wherein the contribution of each voxel to the scattering angle and deflection distance along each axis of deflection accounts both for 2D and 3D incident angles.

23. The method of claim 1, wherein the visual representation allocates a fixed region for each voxel, the fixed region displaying only the most likely scattering density assigned to the respective voxel.

24. The method of claim 23, wherein the visual representation includes a plurality of cross sections of the most likely scattering density map, the most likely scattering density map being a three-dimensional map.

25. The method of claim 24, wherein the cross sections are formed along an axis of deflection of the muon in the scanned volume.

26. The method of claim 24, wherein a scattering density of the most likely scattering density map is represented by hue and luminosity, the luminosity changing monotonously with the scattering density.

27. The method of claim 1, wherein the most likely scattering density map is determined using an EM algorithm or an optimization transfer algorithm that assigns a hidden variable to a contribution of each voxel to a value read in an X-ray pixel.

28. The method of claim 1, where the most likely scattering density map is determined using an iterative algorithm.

29. The method of claim 1, further comprising raising an audible or visual alarm if the most likely scattering density map includes a region of high scattering density.

30. A method of detecting a high atomic number (high-Z) material in a volume, comprising:
    placing a material in a volume to be scanned;
    scanning the volume with a muon detection system to provide detection signals corresponding to muon scan data;
    using the muon scan data, reconstructing an exit momentum and incoming and outgoing tracks of muons that pass through the muon detection system, the incoming track including a first position and first direction of travel of the muons before the muons enter the volume, the outgoing track including a second position and a second direction of travel of the muons after the muons exit the volume, the exit momentum reconstructed for the muons after the muons exit the volume;
    calculating a muon-scattering statistical model using (a) the muon exit momentum and (b) the incoming and outgoing tracks of the muon, wherein calculating the muon-scattering statistical model includes, for each axis of muon deflection in the volume:
        calculating a scattering angle between the incoming track and the outgoing track of the muon;
        calculating a deflection distance of the muon;
        determining a respective uncertainty of the scattering angle and the deflection distance;
        calculating a contribution of each voxel to the scattering angle and the deflection distance;
        determining alternative paths and/or path segments of the muon through the volume; and
        synthesizing the alternative paths into a fuzzy path of the muon, that includes at least one voxel per layer of voxels, and where each voxel includes a respective weight;
    determining a most likely scattering density map according to the muon-scattering statistical model; and
    on a visual image display configured to show a scattering density map, displaying a visual representation of the most likely scattering density map of said material in said volume.

31. A method of detecting a high atomic number (high-Z) material in a volume, comprising:
    scanning the volume with a muon detection system to provide detection signals corresponding to muon scan data;
    using the muon scan data, reconstructing an exit momentum and incoming and outgoing tracks of muons that pass through the muon detection system, the incoming track including a first position and first direction of travel of the muons before the muons enter the volume, the outgoing track including a second position and a second direction of travel of the muons after the muons exit the volume, the exit momentum reconstructed for the muons after the muons exit the volume, wherein reconstructing the exit momentum and the incoming and outgoing tracks includes:

clustering muon detector hits from each of a plurality of detector layers of said muon detection system to form clustered location data;

determining a muon location in each detector layer based on the clustered location data;

estimating the incoming track as a first straight line that passes through a first muon location in a first detector layer and a second muon location in a second detector layer, the first and second detector layers disposed above the volume;

estimating the outgoing track as a second straight line that passes through a third muon location in a third detector layer and a fourth muon location in a fourth detector layer, the third and fourth detector layers disposed below the volume; and determining the exit momentum using (a) scattering angles of the muons in a spectrometer and (b) an absorption of muons in the spectrometer, the spectrometer disposed beneath the fourth detector layer;

calculating a muon-scattering statistical model using (a) the muon exit momentum and (b) the incoming and outgoing tracks of the muon;

determining a most likely scattering density map according to the muon-scattering statistical model; and on a visual image display configured to show a scattering density map, displaying a visual representation of the most likely scattering density map of said material in said volume.

32. The method of claim 31, wherein the exit momentum is further determined using (a) a number of distinct detector hits from the third or fourth detector layer or (b) a width and a spatial structure of an energy deposited in the muon detector hits in the third or fourth detector layer.

* * * * *